(12) United States Patent
Raymond et al.

(10) Patent No.: US 7,026,512 B2
(45) Date of Patent: *Apr. 11, 2006

(54) TERTIARY ALKANOLAMINES CONTAINING SURFACE ACTIVE ALKYL GROUPS

(75) Inventors: William R. Raymond, New Tripoli, PA (US); Juan Jesus Burdeniuc, Macungie, PA (US); Khalil Yacoub, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 110 days.

This patent is subject to a terminal disclaimer.

(21) Appl. No.: 10/731,492

(22) Filed: Dec. 10, 2003

(65) Prior Publication Data
US 2004/0181077 A1 Sep. 16, 2004

Related U.S. Application Data

(63) Continuation-in-part of application No. 10/385,576, filed on Mar. 10, 2003.

(51) Int. Cl.
C07C 215/08 (2006.01)
C07C 215/10 (2006.01)
C07C 215/12 (2006.01)
C07C 215/14 (2006.01)
C07C 215/18 (2006.01)

(52) U.S. Cl. .................... 564/292; 564/295
(58) Field of Classification Search ............... None
See application file for complete search history.

(56) References Cited

U.S. PATENT DOCUMENTS

| | | | |
|---|---|---|---|
| 3,931,430 A | 1/1976 | Tada et al. | |
| 4,007,140 A | 2/1977 | Ibbotson | |
| 4,012,445 A | 3/1977 | Priest et al. | |
| 4,101,470 A | 7/1978 | McEntire | |
| 4,148,762 A | 4/1979 | Koch et al. | |
| 4,296,231 A * | 10/1981 | Gutekunst et al. | 528/93 |
| 4,311,618 A | 1/1982 | Schäfer-Burkhard | |
| 4,644,017 A | 2/1987 | Haas et al. | |
| 4,650,000 A | 3/1987 | Andreasson et al. | |
| 4,710,191 A | 12/1987 | Kwiatek et al. | |
| 4,735,970 A | 4/1988 | Sommerfeld et al. | |
| 4,797,202 A | 1/1989 | Klimpel et al. | |
| 5,124,367 A | 6/1992 | Barker et al. | |
| 5,143,944 A | 9/1992 | Savoca et al. | |
| 5,194,609 A | 3/1993 | Savoca et al. | |
| 5,200,434 A | 4/1993 | Bailey, Jr. et al. | |
| 5,233,039 A | 8/1993 | Listemann et al. | |
| 5,302,303 A | 4/1994 | Clatty et al. | |
| 5,374,486 A | 12/1994 | Clatty et al. | |
| 5,489,618 A * | 2/1996 | Gerkin | 521/128 |
| 5,508,314 A | 4/1996 | Listemann et al. | |
| 5,559,161 A | 9/1996 | Klotz et al. | |
| 5,633,293 A | 5/1997 | Van Court Carr et al. | |
| 6,437,185 B1 | 8/2002 | Walele et al. | |
| 6,525,107 B1 * | 2/2003 | Wendel et al. | 521/115 |

FOREIGN PATENT DOCUMENTS

| | | |
|---|---|---|
| CH | 313 159 A | 3/1956 |
| CH | 313159 | 3/1956 |
| JP | 450119973 B4 | 7/1970 |
| JP | 52018047 B4 | 2/1977 |

OTHER PUBLICATIONS

European Search Report No. 04005139.3-2115 dated Jun. 23, 2004.

* cited by examiner

*Primary Examiner*—Brian Davis
(74) *Attorney, Agent, or Firm*—Michael Leach

(57) ABSTRACT

The present invention relates to novel tertiary alkanolamines useful as catalysts for preparing polyurethane foams and as additives to reduce the dynamic surface tension of aqueous solutions. The tertiary alkanolamines may be represented by formula (I):

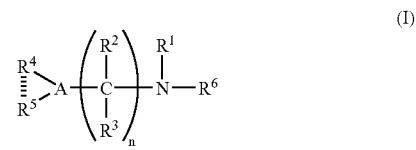

(I)

wherein A, $R^1$–$R^6$, and n are defined herein, and where the tertiary alkanolamine is acid-blocked with a carboxylic acid.

19 Claims, No Drawings

TERTIARY ALKANOLAMINES CONTAINING SURFACE ACTIVE ALKYL GROUPS

CROSS-REFERENCE TO RELATED APPLICATIONS

This application is a continuation-in-part of application Ser. No. 10/385,576 filed 10 Mar. 2003.

BACKGROUND OF THE INVENTION

The present invention relates to the use of novel tertiary alkanolamines prepared by reacting a terminal epoxy compound with a primary or secondary amine. The new tertiary alkanolamines are useful as catalysts for preparing polyurethane foams and as additives to reduce the dynamic surface tension of aqueous solutions.

Polyurethane foams are widely known and used in automotive, housing, and other industries. Polyurethane foams are prepared by reacting a polyisocyanate with a polyol in the presence of various additives. One such additive is a chlorofluorocarbon (CFC) blowing agent, which vaporizes as a result of the reaction exotherm, which causes the polymerizing mass to form a foam. The discovery that chlorofluorocarbons deplete ozone in the stratosphere has resulted in mandates lowering the use of chlorofluorocarbons. The use of water blown foams, in which blowing function is performed by $CO_2$ generated from the reaction of water with a polyisocyanate, has therefore become increasingly important. Tertiary amine catalysts are often used to accelerate the blowing (reaction of water with a polyisocyanate) and gelling (reaction of a polyol with an isocyanate) functions.

The ability of the tertiary amine catalyst to selectively promote either blowing or gelling is an important consideration in selecting a catalyst for preparing a particular polyurethane foam. If a catalyst promotes the blowing reaction too quickly, a substantial portion of the $CO_2$ will be evolved and will bubble out of the formulation before sufficient reaction of the isocyanate with the polyol has occurred, resulting in collapse of the foam and the production of a poor quality foam. On the other hand, if a catalyst promotes the gelling reaction too quickly, a substantial portion of the polymerization will have occurred before sufficient $CO_2$ has been evolved, resulting in insufficient blowing action and the production of a poor quality foam.

Tertiary amine catalysts are generally malodorous and offensive and many are highly volatile due to their low molecular weight. The release of tertiary amine during foam processing may present significant safety and toxicity problems and the release of residual amine during customer handling is undesirable. On the other hand, low vapor pressure-high molecular weight amine catalysts are expected to require very high catalyst usage due to their low N/C ratio making the manufacturing cost very high.

Surprisingly, amine catalysts which contain hydroxyl groups as well as higher-alkyl ($C_6$ or higher) or fatty acid groups have shown an unusual high activity making their usage level relatively modest. Their high molecular weight, reduced volatility and odor can limit the exposure of operators to offensive amine vapors. Furthermore, catalysts which contain hydroxyl functionality can chemically bind into the urethane during the reaction and are not released from the finished product. Catalysts of this type are typically of low to moderate activity and promote both the blowing (water-isocyanate) and the gelling (polyol-isocyanate) reactions to varying extents.

U.S. Pat. No. 4,148,762 discloses the use of the product obtained from reacting N,N-dimethyl-1,3-propanediamine with a $C_1$–$C_{18}$ non-terminal and non-glycidyl epoxy mixture in glycerol to give the aminoalkanol that was further treated with sodium chloroacetate to give a betaine said to be useful in cosmetic applications.

U.S. Pat. No. 4,644,017 discloses diffusion stable amino alkyl ureas having tertiary amino groups said to be useful during the preparation of a polyisocyanate addition product which do not discolor or change the constitution of surrounding materials. Specifically taught are Catalyst A and Catalyst D which are reaction products of dimethylaminopropylamine and urea.

U.S. Pat. No. 4,007,140 discloses the use of N,N'-bis(3-dimethylaminopropyl)urea as a low odor catalyst for preparing polyurethanes and the use of N-(3-dimethylaminopropyl)-formamide as a catalyst to make polyurethane foams.

U.S. Pat. No. 4,012,445 describes the use of beta-amino carbonyl compounds as catalysts for preparing polyurethane foams. The beta-amino part of the catalyst is present as a dialkylamino or a N-morpholino or a N,N'-piperazino heterocyclic nucleus and the carbonyl part is present as an amido or ester.

U.S. Pat. No. 4,735,970 discloses a process for preparing cellular polyurethanes using amine-$CO_2$ adducts, homogeneous mixtures of these adducts, and the use of N-(3-dimethylaminopropyl)-formamide as catalysts to make polyurethane foams.

U.S. Pat. No. 5,200,434 describes the use of amide derivatives of alkylene oxide polyethers and their uses in polyurethane foam formulation.

U.S. Pat. Nos. 5,302,303; 5,374,486 and 5,124,367 disclose that the shelf-life stability of isocyanate-reactive compositions is often adversely affected by the addition of flame-retardants, especially those based on phosphorous, zinc, antimony and aluminum, and that the use of fatty amido-amines stabilizes isocyanate compositions containing flame-retardants.

U.S. Pat. No. 4,710,191 relates to the preparation of polyurethane foams using hydroxyl-quinuclidine derivatives such as 3-hydroxymethyl quinuclidine, 3-methyl-3-hydroxymethyl quinuclidine, and 4-hydroxymethyl quinuclidine.

U.S. Pat. Nos. 5,233,039; 5,194,609; 5,233,039 and 5,143,944 describe a method for making polyurethane foams using 3-quinuclidinol and its derivatives.

U.S. Pat. Nos. 5,559,161; 5,633,293 and 5,508,314 describe a method for making a polyurethane foam using hydroxyl-containing tertiary amines as foaming catalysts. The catalysts composition used were essentially permethylated mono- and/or dialkylene oxide adducts of tris(2-aminoethyl)amine.

U.S. Pat. No. 4,650,000 discloses adducts prepared by the reaction of polyamines with C6–C18 alkyl glycidyl ethers. The adducts are said to be effective surfactants for the formation of microemulsions containing a hydrocarbon oil and aqueous solutions used to treat subterranean rock formations surrounding oil and gas wells. The amine surfactants were utilized in the microemulsions as cationic quaternary ammonium salts.

U.S. Pat. No. 4,797,202 discloses N-(hydrocarbyl)-α,ω-alkanediamines as collectors for the recovery of minerals from mineral ores by froth flotation. In particular, the 1:1 adduct of diethylenetriamine and 2-ethylhexyl glycidyl ether was shown to be effective for copper recovery in the froth flotation of copper sulfide.

CH 313,159 discloses a process for the preparation of stable dye and stripper baths containing positively charged amine additives. The baths contain 1:1 adducts of diamines and polyamines and C8 and greater alkylglycidyl ethers and the corresponding alkylated amines are formed by subsequent reactions with ethylene oxide, dimethyl sulfate, chloroacetic acid and other reagents.

U.S. Pat. No. 4,311,618 discloses the use of a water soluble cleanser concentrate comprising an ionic surfactant, a non-ionic surfactant, an amphoteric dissociating agent and an organic aprotic solvent. Example 5 discloses the hydrochloride salt of the 1:2 adduct of diethylenetriamine and 2-ethylhexyl glycidyl ether.

JP52018047 discloses adducts prepared by the reaction of polyamines and up to 3 C6–C16 alkyl glycidyl ethers which are said to be useful as bactericides.

JP 450119973 discloses adducts prepared by the reaction of polyamines and up to 3 C6–C16 alkyl glycidyl ethers which also contain carboxylate groups which are said to be useful as bactericidal surfactants.

U.S. Pat. No. 3,931,430 discloses the use of the products of diamines and polyamines and C4–C16 glycidyl esters and ethers said to be useful as desensitizers for pressure-sensitive recording sheets. These desensitizers must be soluble in an oil vehicle used to make non-aqueous ink for offset printing.

U.S. Pat. No. 6,437,185 discloses quaternary ammonium compounds prepared salts from alkoxylated polycat 15 reacted with an alpha, beta epoxy alkane. The quaternization takes place with a product such as a diethyl sulfate and the product is said to be useful as a conditioner of hair, fiber, and textile.

SUMMARY OF THE INVENTION

The present invention relates to novel tertiary alkanolamines useful as catalysts for preparing polyurethane foams and as additives to reduce the dynamic surface tension of aqueous solutions. The tertiary alkanolamines may be represented by formula (I):

wherein A represents CH or N;
$R^1$ represents hydrogen and $R^6$ represents —$CH_2C(R^7)(OH)CH_2OR^8$; or
$R^1$ represents

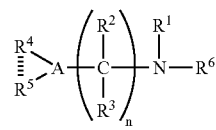

and $R^6$ represents —$CH_2C(R^7)(OH)CH_2OR^8$; or $R^1$ represents —$CH_2C(R^7)(OH)CH_2OR^8$ and $R^6$ represents an alkyl or alkenyl group having $C_4$–$C_{36}$ carbon atoms; or
$R^1$ represents hydrogen and $R^6$ represents —$CH_2C(R^7)(OH)R^8$; or
$R^1$ represents

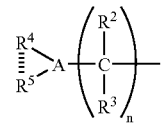

and $R^6$ represents —$CH_2C(R^7)(OH)R^8$; or
$R^1$ represents —$CH_2C(R^7)(OH)R^8$ and $R^6$ represents an alkyl or alkenyl group having $C_4$–$C_{36}$ carbon atoms;
$R^2$ and $R^3$ each represent hydrogen or an alkyl or alkenyl group having $C_1$–$C_6$ carbon atoms;
$R^4$ and $R^5$ each represent an alkyl group having $C_1$–$C_6$ carbon atoms when A represents N; or
$R^4$ and $R^5$ together represent a $C_2$–$C_5$ alkylene group when A represents N; or
$R^4$ and $R^5$ together represent a $C_2$–$C_5$ alkylene group containing $NR^{10}$ or $NR^{11}$ when A is CH or N, where $R^{10}$ is hydrogen or an alkyl group having $C_1$–$C_4$ carbon atoms and $R^{11}$ is an alkyl group having $C_1$–$C_4$ carbon atoms or

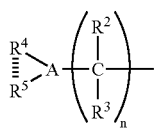

$R^7$ represents hydrogen or an alkyl or alkenyl group having $C_1$–$C_5$ carbon atoms;
$R^8$ represents an alkyl or alkenyl group having $C_4$–$C_{36}$ carbon atoms or —$COR^9$, where $R^9$ represents an alkyl or alkenyl group having $C_3$–$C_{35}$ carbon atoms; and
n is an integer from 1 to 3.

When the tertiary alkanolamines of the invention are used as catalysts in polyurethane applications, the catalysts are typically used in the presence of a gelling catalyst but combinations of blowing and gelling catalysts are also possible. The reactive catalyst compositions contain at least one hydroxyl group that enables the catalyst to react into the polyurethane matrix thereby immobilizing the amine during and after polymerization. These reactive catalysts can be used as gelling catalysts or blowing catalysts with the aid (or not) of complementary tertiary amine blowing or gelling co-catalysts, which may or may not contain reactive functional groups to produce polyurethane foam materials. The reactive catalysts have no amine emissions in the finished product, have low vapor pressures and low odor, and have lower amine concentration and optimum kinetics and physical properties. The appropriate selection of these reactive catalysts in conjunction (or not) with complementary gelling or blowing amine co-catalysts can provide foams with optimum airflows. Good airflow means improved porosity and openness which is an indication of improved dimensional stability of the foam. The surfactant properties of the tertiary alkanolamines help in micronising and stabilizing the foam. While the tertiary alkanolamines act as defoaming surfactants in inks with water based systems, the tertiary alkanolamines will stabilize and promote foam in polyurethane systems.

Another embodiment of the invention provides the reactive catalysts of the present invention as blocked with different acids to yield delay action catalysts. Such acid-blocked catalysts are expected to yield, in addition to the inherent benefits of the present composition, a delay action, which can be of advantage in flexible molded and rigid polyurethane foams.

DETAILED DESCRIPTION OF THE INVENTION

The present invention relates to a compound represented by formula (I):

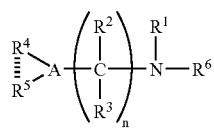

(I)

In formula (I), A represents CH or N.

$R^1$ may represent hydrogen and $R^6$ may represent —$CH_2C(R^7)(OH)CH_2OR^8$; or $R^1$ may represent

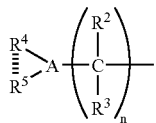

and $R^6$ may represent —$CH_2C(R^7)(OH)CH_2OR^8$; or $R^1$ may represent —$CH_2C(R^7)(OH)CH_2OR^8$ and $R^6$ may represent an alkyl or alkenyl group having $C_4$–$C_{36}$ carbon atoms; or $R^1$ may represent hydrogen and $R^6$ may represent —$CH_2C(R^7)(OH)R^8$; or $R^1$ may represent

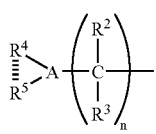

and $R^6$ may represent —$CH_2C(R^7)(OH)R^8$; or $R^1$ may represent —$CH_2C(R^7)(OH)R^8$ and $R^6$ may represent an alkyl or alkenyl group having $C_4$–$C_{36}$ carbon atoms; preferably $R^1$ is hydrogen or

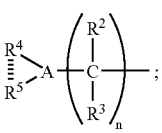

$R^2$ and $R^3$ each represent hydrogen or an alkyl or alkenyl group having $C_1$–$C_6$ carbon atoms; preferably $R^2$ and $R^3$ are hydrogen;

$R^4$ and $R^5$ may each represent an alkyl group having $C_1$–$C_6$ carbon atoms when A represents N; or $R^4$ and $R^5$ together may represent a $C_2$–$C_5$ alkylene group when A represents N; or $R^4$ and $R^5$ together may represent a $C_2$–$C_5$ alkylene group containing $NR^{10}$ or $R^{11}$ when A is CH or N, where $R^{10}$ is hydrogen or an alkyl group having $C_1$–$C_4$ carbon atoms and $R^{11}$ is an alkyl group having $C_1$–$C_4$ carbon atoms or

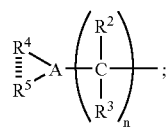

preferably $R^4$ and $R^5$ are alkyl groups having $C_1$–$C_6$ carbon atoms when A represents N;

and preferably $R^4$ and $R^5$ together represent —$CH_2CH_2N(CH_3)CH_2$—;

$R^7$ represents hydrogen or an alkyl or alkenyl group having $C_1$–$C_5$ carbon atoms;

preferably $R^7$ represents hydrogen;

$R^8$ represents an alkyl or alkenyl group having $C_4$–$C_{36}$ carbon atoms or —$COR^9$;

where $R^9$ represents an alkyl or alkenyl group having $C_3$–$C_{35}$ carbon atoms;

preferably $R^8$ represents an alkyl or alkenyl group having $C_4$–$C_{22}$ carbon atoms or —$COR^9$;

preferably $R^9$ represents an alkyl or alkenyl group having $C_3$–$C_{22}$ carbon atoms;

n is an integer from 1 to 3; preferably from 2 to 3.

The compounds and methods of the present invention are more fully described in copending patent application entitled "Tertiary Alkanolamine Polyurethane Catalysts Derived From Long Chain Alkyl and Fatty Carboxylic Acids", filed by applicants concurrently with the present patent application and assigned to the assignee of this application, which application is hereby incorporated by reference.

Preferably, the tertiary alkanolamine compound is selected from the group consisting of N,N-bis-(3-dimethylaminopropyl)-N-(2-hydroxypropyl-octadecyl ether) amine, N-(3-dimethylaminopropyl)-N-(2-hydroxypropyl-octadecyl ether) amine, N,N-bis-(3-dimethylaminopropyl)-N-(2-hydroxypropyl-hexadecyl ether) amine, N-(3-dimethylaminopropyl)-N-(2-hydroxypropyl-hexadecyl ether) amine, N,N-bis-(3-dimethylaminopropyl)-N-(2-hydroxypropyl-tetradecyl ether) amine, N-(3-dimethylaminopropyl)-N-(2-hydroxypropyl-tetradecyl ether) amine, N,N-bis-(3-dimethylaminopropyl)-N-(2-hydroxypropyl-dodecyl ether) amine, N-(3-dimethylaminopropyl)-N-(2-hydroxypropyl-dodecyl ether) amine, N,N-bis-(3-dimethylaminopropyl)-N-(2-hydroxypropyl-decyl ether) amine, N-(3-dimethylaminopropyl)-N-(2-hydroxypropyl-decyl ether) amine, N,N-bis-(3-dimethylaminopropyl)-N-(2-hydroxypropyl-octyl ether) amine, N-(3-dimethylaminopropyl)-N-(2-hydroxypropyl-octyl ether) amine, N,N-bis-(3-dimethylaminopropyl)-N-(2-hydroxypropyl-2-ethylhexyl ether) amine, N-(3-dimethylaminopropyl)-N-(2-hydroxypropyl-2-ethylhexyl ether) amine, N,N-bis-(3-dimethylaminopropyl)-N-(2-hydroxypropyl-hexyl ether) amine, N-(3-dimethylaminopropyl)-N-(2-hydroxypropyl-hexyl ether) amine, N,N-bis-(3-dimethylaminopropyl)-N-(2-hexanol) amine, N-(3-dimethylaminopropyl)-N-(2-hexanol) amine, N,N-bis-(3-dimethylaminopropyl)-N-(2-octanol) amine, N-(3-dimethylaminopropyl)-N-(2-octanol) amine, N,N-bis-(3- dimethylaminopropyl)-N-(2-decanol) amine, N-(3-dimethylaminopropyl)-N-(2-decanol) amine, N,N-bis-(3-dimethylaminopropyl)-N-(2-dodecanol) amine, N-(3-dimethylaminopropyl)-N-(2-dodecanol) amine, N,N-bis-(3-dimethylaminopropyl)-N-(2-tetradecanol) amine, N-(3-dimethylaminopropyl)-N-(2-tetradecanol) amine, N,N-bis-(3-dimethylaminopropyl)-N-(2-hexadecanol) amine, N-(3-dimethylaminopropyl)-N-(2-hexadecanol) amine, N,N-bis-(3-dimethylaminopropyl)-N-(2-octadecanol) amine, N-(3-dimethylaminopropyl)-N-(2-octadecanol) amine; N,N-bis-(3-dimethylaminopropyl)-N-(2-hydroxypropyl butyl ether) amine; and N,N-bis-(3-dimethylaminopropyl)-N-(2-hydroxypropyl-neodecanoic ester) amine.

More preferably the compound is selected from the group consisting of N,N-bis-(3-dimethylaminopropyl)-N-(2-hydroxypropyl-octadecyl ether) amine, N-(3-dimethylaminopropyl)-N-(2-hydroxypropyl-octadecyl ether) amine, N,N-bis-(3-dimethylaminopropyl)-N-(2-hydroxypropyl-hexadecyl ether) amine, N-(3-dimethylaminopropyl)-N-(2-hydroxypropyl-hexadecyl ether) amine, N,N-bis-(3-dimethylaminopropyl)-N-(2-hydroxypropyl-tetradecyl ether) amine, N-(3-dimethylaminopropyl)-N-(2-hydroxypropyl-tetradecyl ether) amine, N,N-bis-(3-dimethylaminopropyl)-N-(2-hydroxypropyl-dodecyl ether) amine, N-(3-dimethylaminopropyl)-N-(2-hydroxypropyl-dodecyl ether) amine, N,N-bis-(3-dimethylaminopropyl)-N-(2-hydroxypropyl-decyl ether) amine, N-(3-dimethylaminopropyl)-N-(2-hydroxypropyl-decyl ether) amine, N,N-bis-(3-dimethylaminopropyl)-N-(2-hydroxypropyl-octyl ether) amine, N-(3-dimethylaminopropyl)-N-(2-hydroxypropyl-octyl ether) amine, N,N-bis-(3-dimethylaminopropyl)-N-(2-hydroxypropyl-2-ethylhexyl ether) amine, N-(3-dimethylaminopropyl)-N-(2-hydroxypropyl-2-ethylhexyl ether) amine, N,N-bis-(3-dimethylaminopropyl)-N-(2-hydroxypropyl-hexyl ether) amine, N-(3-dimethylaminopropyl)-N-(2-hydroxypropyl-hexyl ether) amine; N,N-bis-(3-dimethylaminopropyl)-N-(2-hydroxypropyl butyl ether) amine; and N,N-bis-(3-dimethylaminopropyl)-N-(2-hydroxypropyl-neodecanoic ester) amine.

Most preferably, the compound is selected from the group consisting of N,N-bis-(3-dimethylaminopropyl)-N-(2-hydroxypropyl butyl ether) amine; N,N-bis-(3-dimethylaminopropyl)-N-(2-hydroxypropyl-2-ethylhexyl ether) amine; N,N-bis-(3-dimethylaminopropyl)-N-(2-hydroxypropyl-tetradecyl ether) amine; N,N-bis-(3-dimethylaminopropyl)-N-(2-hydroxypropyl-dodecyl ether) amine; and N,N-bis-(3-dimethylaminopropyl)-N-(2-hydroxypropyl-neodecanoic ester) amine.

The tertiary alkanolamine compounds can be prepared by reacting a terminal epoxy compound with the corresponding tertiary alkylamine in the appropriate molar ratios at temperatures from about 50° C. to about 250° C., preferably from about 80° C. to about 150° C. (where $R^6$ represents —$CH_2C(R^7)(OH)CH_2OR^8$).

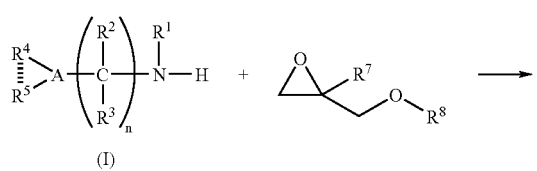
(I)

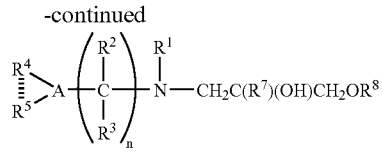

Since the reaction is exothermic, it is preferable to add the epoxy compound to the tertiary alkylamine at a slow rate (over 1–2 hours) since the heat evolved is derived from opening the epoxy ring. Adding the tertiary alkylamine to the epoxy compound could produce an unsafe situation where a large exotherm would be generated, particularly in the presence of a tertiary amine, which catalyzes the opening of the epoxy ring.

The tertiary alkanolamine compounds of the present invention can be used in catalyst compositions to catalyze polyurethane applications, i.e., the reaction between an isocyanate functionality and an active hydrogen-containing compound, i.e., an alcohol, a polyol, an amine, or water. The catalyst compositions also catalyze the urethane (gelling) reaction of polyol hydroxyl groups with isocyanate to make polyurethanes and the blowing reaction of water with isocyanate to release carbon dioxide for making foamed polyurethanes.

The flexible polyurethane foam products are prepared using any suitable organic polyisocyanates known in the art including, for example, hexamethylene diisocyanate, phenylene diisocyanate, toluene diisocyanate (TDI) and 4,4'-diphenylmethane diisocyanate (MDI). Especially suitable are the 2,4- and 2,6-TDI's individually or together as their commercially available mixtures. Other suitable isocyanates are mixtures of diisocyanates known commercially as "crude MDI", marketed as PAPI by Dow Chemicals, which contains about 60% of 4,4'-diphenylmethane diisocyanate along with other isomeric and analogous higher polyisocyanates. Also suitable are "prepolymers" of these polyisocyanates comprising a partially prereacted mixture of a polyisocyanate and a polyether or polyester polyol.

Illustrative examples of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and similar low molecular weight polyols.

In the practice of this invention, a single high molecular weight polyether polyol may be used. Also, a mixture of high molecular weight polyether polyols such as mixtures of di- and tri-functional materials and/or different molecular weight or different chemical composition materials may be used.

Useful polyester polyols include those produced by reacting a dicarboxylic acid with an excess of a diol, for example, adipic acid with ethylene glycol or butanediol, or reaction of a lactone with an excess of a diol such as caprolactone with propylene glycol.

In addition to the polyester and polyethers polyols, the master batches, or premix compositions, frequently contain a polymer polyol. Polymer polyols are used in polyurethane foams to increase the foam's resistance to deformation, i.e., to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol, which is formed by the in-situ polymerization of TDI and alkanolamine in the polyol. Depending upon the load-bearing requirements, polymer polyols may comprise 20–80% of the polyol portion of the master batch.

Other typical agents found in the polyurethane foam formulations include chain extenders such as ethylene glycol and butane diol; cross-linkers such as diethanolamine, diisopropanolamine triethanolamine and tripropanolamine; blowing agents such as water, CFCs, HCFCs, HFCs, pentane, and the like; and cell stabilizers such as silicone surfactants.

A general polyurethane flexible foam formulation according to the invention would comprise the following components in parts by weight (pbw):

| Polyol | 20–100 |
| Polymer Polyol | 80–0 |
| Silicone Surfactant | 1–2.5 |
| Blowing agent | 2–4.5 |
| Crosslinker | 0.5–2 |
| Catalyst | 0.25–2 |
| Isocyanate Index | 70–115 |

The tertiary alkanolamine compounds can be used in conjunction with a gelling catalyst, such as a tertiary amine or a suitable transition metal catalyst, and/or a blowing catalyst depending upon the processing advantages desired.

Examples of suitable tertiary amine gelling catalysts include, but are not restricted to, diazabicyclooctane (triethylenediamine), supplied commercially as DABCO 33LV® catalyst by Air Products & Chemicals Inc., quinuclidine and substituted quinuclidines, substituted pyrrolidines and pyrrolizidines. Examples of suitable tertiary amine blowing catalysts include, but are not restricted to, bis-dimethylaminoethyl ether, commercially supplied as DABCO® BL11 catalyst by Air Products and Chemicals, Inc., pentamethyldiethylenetriamine and related compositions, higher permethylated polyamines, 2-[N-(dimethylaminoethoxyethyl)-N-methylamino]ethanol and related structures, alkoxylated polyamines, imidazole-boron compositions and amino propyl-bis(aminoethyl)ether compositions.

In another embodiment of the invention, the reactive catalysts of the present invention can be blocked with different acids to yield delay action catalysts. Such acid-blocked catalysts are expected to yield, in addition to the inherent benefits of the present composition, a delay action, which can be of advantage in flexible molded and rigid polyurethane foams. The acid-blocked catalysts can simply be obtained by reacting the catalyst composition with carboxylic acids such as formic acid, acetic acid, 2-ethylhexanoic acid, gluconic acid, N-(2-hydroxyethyl)-iminodiacetic acid, and the like as is well known in the art. The salts obtained are not catalytically active and consequently they do not activate the polyurethane/blowing reactions until the temperature is sufficiently high that dissociation of the salts start to occur. Acid-blocked catalysts of the present invention can find their main applications in molded flexible and rigid foams where delaying the onset of the reaction is desired. This delay causes the viscosity to increase slowly allowing the proper filling of a mold while maintaining the overall molding time as short as possible to maintain maximum productivity.

A catalytically effective amount of the catalyst composition comprising the tertiary alkanolamine compound and a tertiary amine gelling or blowing catalyst may be used in the polyurethane formulation. More specifically suitable amounts of the catalyst composition may range from about 0.01 to 10 parts by wt per 100 parts polyol (pphp) in the polyurethane formulation, preferably 0.05 to 2 pphp.

The catalyst composition may be used in combination with, or also comprise, other tertiary amines, organotin or carboxylate urethane catalysts well known in the urethane art.

The present invention provides novel tertiary alkanolamines represented by formula (I) prepared by reacting a terminal epoxy compound with a primary or secondary amine. The present invention also provides a method for preparing a polyurethane foam which comprises reacting an organic polyisocyanate and a polyol in the presence of water as a blowing agent, a cell stabilizer, and a tertiary amine amide catalyst composition represented by formula (I). The present invention further provides the improvement of enabling the reaction between water and isocyanate to cause blowing of the foam while maintaining and controlling the physical properties of the foam which comprises using a tertiary amino alkyl amide catalyst composition represented by formula (I).

Although the present invention has been described as useful for preparing flexible polyurethane foams, the invention may also be employed to prepare semi-flexible and rigid polyurethane foams. Rigid polyurethane foams can be distinguished from flexible polyurethane foams by the presence of higher isocyanurate levels in the rigid foam. Flexible foams typically use polymer polyol as part of the overall polyol content in the foam composition, along with conventional triols of 4000–5000 weight average molecular weight (Mw) and hydroxyl number (OH#) of 28–35. In contrast, rigid polyurethane foam compositions use 500–1000 Mw polyol with 3–8 hydroxyl functionalities and OH# of 160–700. Rigid foams can also be distinguished from the flexible foams by the isocyanate (NCO) index of the foam composition. Rigid foam compositions typically use a 100–300 NCO index whereas flexible foam compositions typically require a 70–115 NCO index.

A general polyurethane rigid insulating foam formulation containing the catalyst composition according to the invention would comprise the following components in parts by weight (pbw):

| Polyol | 100 |
| Silicone Surfactant | 1–3 |
| Blowing Agent | 0–50 |
| Water | 0–8 |
| Catalyst | 0.5–15 |
| Isocyanate Index | 80–300 |

For making lamination (insulation board) and appliance foams the NCO index is typically 100–300; for making open cell foam the NCO index is typically 100–120 and the foam is usually all water blown.

Semiflexible molded foams have been utilized for many applications in the automotive area. The major applications are instrument panels and interior trims. A typical semiflexible foam formulation containing the catalyst composition according to the invention comprise the following components in parts by weight (pbw):

| | |
|---|---|
| SPECFLEX NC 630 Polyol | 80.0 |
| SPECFLEX NC 710 | 20.0 |
| Copolymer | |
| Cross-linker | 1.5 |
| Water | 2.2 |
| Catalyst | 0.5–10 |
| Black Colorant | 0.3 |
| Adhesion Promoter | 2.0 |
| Cell Opener | 1.0 |
| Polymeric MDI, Index | 105 |

The two main components are the base polyol and copolymer polyol (CPP). The base polyol is utilized at levels between 70–100%. The molecular weight of base polyols range from 4500 to 6000 for triols and 2000 to 4000 for diols. Ethylene-oxide-capped polyether polyols have replaced most polyester polyols as the base polyol. The primary hydroxyl content is usually grater than 75% and the capping range is typically 10–20%. The other major component is CPP, which are used at levels of 0 to 20%. The base polyol and CPP are blended with low molecular weight cross linkers to build hardness and promote faster demolding. The level of cross linker varies depending on the hardness requirement of the finished part. Water levels are chosen to give free rise densities from 3 to 6 pounds. Cell openers are also utilized in semiflexible foams to reduce the internal foam pressure during the cure cycle and thus reduce pressure-relief voids and "parting lines". Adhesion promoters can be added, depending upon the quality of the vinyl skin, to improve the adhesion between the polyurethane foam and the vinyl skin. The use of the catalyst composition of the present invention can reduce the discoloration of the vinyl skin typically observed with conventional amine catalysts because the hydroxyl group can react with the isocyanate to form a covalent bond with the polyurethane polymer.

Throughout this disclosure, applicant will suggest various theories or mechanisms by which applicant believes the present methods function. While applicant may offer various mechanisms to explain the present invention, applicant does not wish to be bound by theory. These theories are suggested to better understand the present invention but are not intended to limit the effective scope of the claims.

Throughout this application, various publications have been referenced. The disclosures in these publications are incorporated herein by reference in order to more fully describe the state of the art.

The present invention is further illustrated by the following examples, which are presented for purposes of demonstrating, but not limiting, the preparation of the compounds and compositions of this invention.

EXAMPLES

Example 1

Reaction between N,N-bis-(3-dimethylaminopropyl)-amine (Polycat®-15) and butyl glycidyl ether (EPODIL® 741) to yield N,N-bis-(3-dimethylaminopropyl)-N-(2-hydroxypropyl butyl ether) amine N,N-bis-(3-dimethylaminopropyl)-amine (54.3 g, 0.29 mol) was placed into a 500 ml three necked round bottom flask equipped with a Teflon® coated magnetic stir bar and a pressure equalizing dropping funnel. The amine was heated to 80° C. under nitrogen and butyl glycidyl ether (45 g, 0.29 mol) was slowly added over a period of 30 minutes. A mild exotherm was observed during the addition that caused the temperature to rise to about 84° C. At the end of the addition, the liquid was heated to 120° C. and maintained at that temperature for about 30 minutes yielding 99.29 g of product.

Example 2

Reaction between N,N-bis-(3-dimethylaminopropyl)-amine (Polycat®-15) and 2-ethylhexyl glycidyl ether (EPODIL® 746) to Yield N,N-bis-(3-dimethylaminopropyl)-N-(2-hydroxypropyl-2-ethylhexyl ether) amine N,N-bis-(3-dimethylaminopropyl)-amine (52.8 g, 0.28 mol) was placed into a 500 ml three necked round bottom flask equipped with a Teflon® coated magnetic stir bar and a pressure equalizing dropping funnel. The amine was heated to 80° C. under nitrogen and 2-ethylhexyl glycidyl ether (50 g, 0.29 mol) was slowly added over a period of 30 minutes. A mild exotherm was observed during the addition that caused the temperature to rise to about 88° C. At the end of the addition, the liquid was heated to 120° C. and maintained at that temperature for about 30 minutes yielding 102.8 g of product.

Example 3

Reaction between N,N-bis-(3-dimethylaminopropyl)-amine (Polycat® 15) and alkyl (C12–C14) glycidyl ether (EPODIL® 748) to yield N,N-bis-(3-dimethylaminopropyl)-N-(2-hydroxypropyl-tetradecyl ether) amine and N,N-bis-(3-dimethylaminopropyl)-N-(2-hydroxypropyl-dodecyl ether) amine N,N-bis-(3-dimethylaminopropyl)-amine (51.9 g, 0.28 mol) was placed into a 500 ml three necked round bottom flask equipped with a Teflon® coated magnetic stir bar and a pressure equalizing dropping funnel. The amine was heated to 80° C. under nitrogen and alkyl (C12–C14) glycidyl ether (75 g, 0.28 mol) was slowly added over a period of 30 minutes. A mild exotherm was observed during the addition that caused the temperature to rise to about 84° C. At the end of the addition, the liquid was heated to 120° C. and maintained at that temperature for about 30 minutes yielding 126.9 g of product.

Example 4

Reaction between N,N-bis-(3-dimethylaminopropyl)-amine (Polycat®-15) and Cardura®E-10 to yield N,N-bis-(3-dimethylaminopropyl)-N-(2-hydroxypropyl-neodecanoic ester) amine N,N-bis-(3-dimethylaminopropyl)-amine (52.36 g, 0.28 mol) was placed into a 500 ml three necked round bottom flask equipped with a Teflon® coated magnetic stir bar and a pressure equalizing dropping funnel. The amine was heated to 80° C. under nitrogen and Cardura®E-10 (70 g, 0.28 mol) was slowly added over a period of 30 minutes. A mild exotherm was observed during the addition that caused the temperature to rise to about 84° C. At the end of the addition, the liquid was heated to 120° C. and maintained at that temperature for about 30 minutes yielding 126.9 g of product. Cardura®E-10 is a commercially available gycidyl ester of Versatic acid. It is a synthetic, saturated monocarboxylic acid mixture of highly branched C10 isomers. The structure where at least one of the alkyl groups is a methyl.

Example 5

Rate of Rise of Foams Made with Different Polycat®-15/EPODIL® Adducts

In this example, polyurethane foams were prepared in a conventional manner. The polyurethane formulation in parts by weight was:

| COMPONENT | PARTS |
|---|---|
| ARCOL E848[1] | 50.00 |
| ARCOL E851[2] | 50.00 |
| WATER | 2.34 |
| DABCO ® DC 5043[3] | 0.75 |
| DEOA-LF[4] | 1.76 |
| DABCO 33LV ®[5] | 0.25 |
| DABCO ® BL-11[6] | 0.10 |
| TDI | 30.25 |
| Index | 100 |

[1–2] commercially available polyols;
[3] commercial silicon surfactant supplied by Air Products & Chemicals;
[4] Cross-linker;
[5] DABCO 33LV ® is a commercially available catalysts supplied by Air Products & Chemicals (33% solution of triethylenediamine in dipropylene glycol);
[6] DABCO ® BL-11 is a commercially available catalyst supplied by Air Products & Chemicals (70% solution of bis-dimethylaminoethylether in dipropylene glycol)

For each foam, the catalyst was added to 158 g of the above premix in a 32 oz (951 ml) paper cup and the formulation was mixed for 10 sec at 6,000 RPM using an overhead stirrer fitted with a 2 in (5.1 cm) diameter stirring paddle. Sufficient TDI 80 was added to make a 100 index foam [index=(mole NCO/mole of active hydrogen)×100] and the formulation was mixed well for 6 sec at 6,000 RPM using the same stirrer. The 32 oz cup was dropped through a hole in the bottom of a 128 oz (3804 ml) paper cup on a stand. The hole was sized to catch the lip of the 32 oz cup. The total volume of the foam container was 160 oz (4755 ml). Foams approximated this volume at the end of the foam forming process. Maximum foam height was recorded.

| Run | DABCO 33LV ® | DABCO ® BL-11 | DABCO ® NE1060[1] | TEXACAT ® ZF-10[2] | POLYCAT ® PC-15 and Epodil ® 748[3] | POLYCAT ® PC-15 and Epodil ® 746[4] | POLYCAT ® PC-15 and Epodil ® 741[5] |
|---|---|---|---|---|---|---|---|
| 1 | 0.25 | 0.1 | | | | | |
| 2 | | | 0.56 | 0.16 | | | |
| 3 | | | 0.70 | | 0.50 | | |
| 4 | | | 0.70 | | | 0.50 | |
| 5 | | | 0.79 | | | | 0.50 |

| Run | Cream | Cup1 | String Gel | Full Rise |
|---|---|---|---|---|
| 1 | 8.40 | 16.70 | 65.30 | 100.1 |
| 2 | 8.10 | 14.90 | 69.90 | 96.40 |
| 3 | 8.70 | 15.70 | 66.20 | 87.40 |
| 4 | 8.30 | 15.70 | — | 94.80 |
| 5 | 8.20 | 15.50 | 64.60 | 83.90 |

[1] DABCO ® NE1060 is a commercially available catalyst supplied by Air Products & Chemicals. The catalysts is a 75% dipropylene glycol solution of N-(3-dimethylaminopropyl)-urea (87%) and N,N'-bis-(3-dimethylamino)-urea (13%);
[2] TEXACAT ® ZF-10 is a commercially available catalysts based on 2-[N-(dimethylaminoethoxyethyl)-N-methylamino]ethanol;
[3] Epodil ® 748 is a commercially available epoxy product supplied by Air Products & Chemicals. The product is mainly composed of alkyl (C12–C14) glycidyl ether;
[4] Epodil ® 746 is a commercially available epoxy product supplied by Air Products & Chemicals. The product is mainly composed of 2-ethyl-hexyl glycidyl ether;
[5] Epodil ® 741 is a commercially available epoxy product supplied by Air Products & Chemicals. The product is mainly composed of butyl glycidyl ether.

| PARAMETER | DABCO 33LV ®/ DABCO ® BL-11 | POLYCAT ® 15 and Epodil ® 748 | POLYCAT ® 15 and Epodil ® 746 | POLYCAT ® 15 and Epodil ® 741 |
|---|---|---|---|---|
| PPHP | 0.12 | 0.20 | 0.20 | 0.20 |
| MOLES* × $10^3$ | 0.80 | 0.90 | 1.08 | 1.26 |
| MOLECULAR WEIGHT | — | 429–457 | 373 | 317 |
| MIXING TIME [s] | 12 | 12 | 12 | 12 |
| TEST TIME [s] | 300 | 300 | 300 | 300 |

-continued

| PARAMETER | DABCO 33LV ®/ DABCO ® BL-11 | POLYCAT ® 15 and Epodil ® 748 | POLYCAT ® 15 and Epodil ® 746 | POLYCAT ® 15 and Epodil ® 741 |
|---|---|---|---|---|
| RISE HEIGHT [mm] | 258.4 | 259.4 | 263.4 | 258.9 |
| RISE TIME [s] | 130.4 | 139.2 | 160.3 | 137.1 |
| MAX HEIGHT [mm] | 263.7 | 264.7 | 268.8 | 264.1 |
| FINAL HEIGHT [mm] | 263.0 | 263.6 | 267.2 | 262.6 |
| SHRINKAGE [%] | 0.3 | 0.4 | 0.6 | 0.7 |

*moles of catalytically active nitrogen

The data shows a good rate match between the industry standard (DABCO 33LV®/DABCO®BL-11) and the different Polycar®-15/Epodil adducts. Most surprisingly, the data shows that the same catalyst usage is required for all Polycate®-15/EPODIL® adducts even though there is a substantial difference in their sizes and molecular weights. Thus, the Me₂N— groups are presumably more active in the Polycat®-15/EPODIL®748 than in the other adducts.

Under these circumstances, the highest molecular weight catalysts has the advantage that amine emissions in finish products are going to be greatly reduced. Thus, the low vapor pressure, the low odor, the presence of a secondary hydroxyl group capable of immobilizing the amine during/after polymerization and the lower concentration of amine in Polycat®-15/EPODIL®748 adduct are some of the advantages offer by this new product.

Example 6

Rate of Rise of Foams Made with Polycat®-15-Epodil® 748 Adducts

The following data provides a comparison between DABCO®BLV (industry standard) and the Polycat®-15-EPODIL® 748 adducts prepared according to the procedures of example 4 and 5.

Good kinetic match was obtained with both Polycat®-15 derivatives requiring relatively modest catalyst loadings when the Polycate®-15/alkyl (C12–C14) glycidyl ether mono-adduct prepared in example 4 was used. The example shows that the catalytic activity of the M₂N— group did not increase in going from the mono- to the bis-adduct because the same number of moles were required to obtain rate match.

Example 7

Comparison between the Physical Properties of Foams Made with Dabco®BLV Industry Standard and with Polycat®-15-Epodil® 748 Adduct This example provides a comparison between the physical properties of foams made with BLV (industry standard) and DMAPA-EPODIL®748. Larger foams (scale factor=3.2) were prepared using the following formulation:

| COMPONENT | PARTS |
|---|---|
| VORANOL 3512A[1] | 100.00 |
| WATER | 4.60 |
| DABCO ® DC 5982[2] | 0.90 |
| AMINE CATALYST[3] | VARIABLE |
| DABCO ® T-10[4] | VARIABLE: 0.52–0.32 |

| PARAMETER | DABCO ® BLV | Polycat ® 15-EPODIL ® 748 FROM Example 4 | Polycat ® 15-EPODIL ® 748 FROM Example 5 | Polycat ® 15-EPODIL ® 748 FROM Example 5 |
|---|---|---|---|---|
| PPHP | 0.12 | 0.80 | 1.40 | 1.60 |
| MOLES* × 10³ | 0.80 | 2.0 | 2.0 | 2.0 |
| MIXING TIME [s] | 12 | 12 | 12 | 12 |
| TEST TIME [s] | 300 | 300 | 300 | 300 |
| RISE HEIGHT [mm] | 294.8 | 307.2 | 308.3 | 302.8 |
| RISE TIME [s] | 104.5 | 128.6 | 124.9 | 103.3 |
| MAX HEIGHT [mm] | 300.6 | 313.2 | 314.3 | 308.6 |
| FINAL HEIGHT [mm] | 299.3 | 311.0 | 312.6 | 306.6 |

*moles of catalytically active nitrogen

-continued

| COMPONENT | PARTS |
|---|---|
| TDI | 56.20 |
| Index | 108 |

[1] polyol;
[2] commercial silicon surfactant supplied by Air Products & Chemicals;
[3] Standard is DABCO ® BLV, a commercially available catalysts supplied by Air Products & Chemicals composed of 75 wt. % of DABCO 33LV ® (a 33% solution of triethylenediamine in dipropylene glycol) and 25 wt. % of DABCO ® BL-11 (70% solution of bis-dimethylaminoethylether in dipropylene glycol);
[4] a commercially available tin catalyst supplied by Air Products & Chemicals.

For each foam, the catalyst was added to 339.2 g of the above premix in a 32 oz (951 ml) paper cup and the formulation was mixed for 10 sec at 6,000 RPM using an overhead stirrer fitted with a 2 in (5.1 cm) diameter stirring paddle. Sufficient TDI 80 was added to make a 108 index foam [index=(mole NCO/mole of active hydrogen)×100] and the formulation was mixed well for 6 sec at 6,000 RPM using the same stirrer. The content was poured into a 3.5 gallon container. Foams approximated this volume at the end of the foam forming process. Maximum foam height was recorded and the physical properties evaluated. In the case of air flows and densities, the foams were cut in three sections of equal length top, middle and bottom and the these properties were measured on each section to compare air flow and density distribution across the length of the foam.

DABCO ® T-10 LEVEL: 0.52 PPHP

| Catalyst | Air Flow (SCFM) | Density (lb/scft) | Average Tear Strength (lbf) | Average Tensile Stength (psi) | Average Break Elongation % |
|---|---|---|---|---|---|
| DABCO ® BLV | Top: 2.96 ± 0.16 Middle: 2.43 ± 0.01 Bottom: 1.36 ± 0.16 | Top: 1.278 ± 0.032 Middle: 1.346 ± 0.01 Bottom: 1.521 ± 0.053 | 2.19 ± 0.26 | 11.56 ± 0.37 | 137.25 ± 4.15 |
| Polycat ® 15/ EPODIL ® 748 | Top: 3.26 ± 0.08 Middle: 2.50 ± 0.20 Bottom: 1.19 ± 0.03 | Top: 1.295 ± 0.024 Middle: 1.366 ± 0.019 Bottom: 1.525 ± 0.005 | 2.17 ± 0.20 | 11.23 ± 0.69 | 129.98 ± 22.99 |

DABCO ® T-10 LEVEL: 0.42 PPHP

| Catalyst | Air Flow (SCFM) | Density (lb/scft) | Average Tear Strength (lbf) | Average Tensile Stength (psi) | Average Break Elongation % |
|---|---|---|---|---|---|
| DABCO ® BLV | Top: 4.20 ± 0.01 Middle: 3.57 ± 0.48 Bottom: 2.66 ± 0.47 | Top: 1.308 ± 0.015 Middle: 1.358 ± 0.025 Bottom: 1.554 ± 0.008 | 2.07 ± 0.10 | 10.22 ± 0.30 | 117.56 ± 9.49 |
| Polycat15 ®/ EPODIL ® 748 | Top: 4.62 ± 0.12 Middle: 4.02 ± 0.23 Bottom: 2.84 ± 0.06 | Top: 1.297 ± 0.02 Middle: 1.371 ± 0.019 Bottom: 1.503 ± 0.001 | 1.97 ± 0.23 | 10.05 ± 0.38 | 119.42 ± 7.64 |

| Catalyst | Air Flow (SCFM) | Density (lb/scft) | Average Tear Strength (lbf) | Average Tensile Stength (psi) | Average Break Elongation % |
|---|---|---|---|---|---|
| DABCO® BLV | Top: 5.46 ± 0.19 Middle: 5.05 ± 0.01 Bottom: 3.73 ± 0.07 | Top: 1.324 ± 0.004 Middle: 1.377 ± 0.017 Bottom: 1.545 ± 0.014 | 2.00 ± 0.19 | 9.75 ± 0.33 | 116.94 ± 8.43 |
| Polycat15®/ EPODIL® 748 | Top: 6.0 ± 0.05 Middle: 5.64 ± 0.25 Bottom: 4.84 ± 0.12 | Top: 1.297 ± 0.002 Middle: 1.296 ± 0.003 Bottom: 1.422 ± 0.012 | 1.95 ± 0.12 | 10.87 ± 1.02 | 135.70 ± 23.06 |

DABCO® T-10 LEVEL: 0.32 PPHP

Thus, the physical properties of the foams made with DABCO®BLV and Polycat®15/EPODIL®748 are very similar. At lower tin levels, Polycat®15/EPODIL®748 seem to provide foams with better air flows than the standard without sacrificing tear and tensile strength.

Example 8

Dynamic Surface Tension of Aqueous Solutions Containing Different Polycat®15/Epodil® Adducts In this example, the different Polycat®15/EPODIL® adducts were dissolved in water and the dynamic surface tension were measured. The data is summarized below showing a comparison among the different Polycat®15/Epodil® adducts.

| Additive-Amount wt. % | 0.1 b/s | 1.0 b/s | 6.0 b/s | 10.0 b/s | 20.0 b/s |
|---|---|---|---|---|---|
| Polycat ® 15/Epodil ® 741-0.1 wt. % | 42.7 | 46.7 | 48.9 | 49.9 | 50.9 |
| Polycat ® 15/Epodil ® 741-0.3 wt. % | 39.9 | 43.9 | 46.7 | 47.5 | 49.5 |
| Polycat ® 15/Epodil ® 746-0.1 wt. % | 30.0 | 36.0 | 39.4 | 41.5 | 43.5 |
| Polycat ® 15/Epodil ® 748-0.1 wt. % | 31.9 | 32.9 | 36.2 | 36.9 | 37.4 |
| Polycat ® 15/Cardura ® E10-0.1 wt. % | 32.4 | 36.0 | 39.3 | 40.8 | 42.1 |

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

The invention claimed is:
1. A compound represented by formula (I):

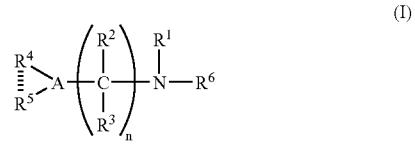

wherein A represents CH or N;
R$^1$ represents hydrogen and R$^6$ represents —CH$_2$C(R$^7$)(OH)CH$_2$OR$^8$; or
R$^1$ represents

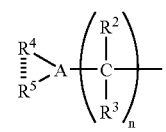

and R$^6$ represents —CH$_2$C(R$^7$)(OH)CH$_2$OR$^8$; or
R$^1$ represents —CH$_2$C(R$^7$)(OH)CH$_2$OR$^8$ and R$^6$ represents an alkyl or alkenyl group having C$_4$–C$_{36}$ carbon atoms; or
R$^1$ represents hydrogen and R$^6$ represents —CH$_2$C(R$^7$)(OH)R$^8$; or
R$^1$ represents

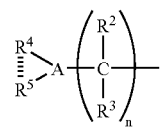

and R$^6$ represents —CH$_2$C(R$^7$)(OH)R$^8$; or
R$^1$ represents —CH$_2$C(R$^7$)(OH)R$^8$ and R$^6$ represents an alkyl or alkenyl group having C$_4$–C$_{36}$ carbon atoms;
R$^2$ and R$^3$ each represent hydrogen or an alkyl or alkenyl group having C$_1$–C$_6$ carbon atoms;
R$^4$ and R$^5$ each represent an alkyl group having C$_1$–C$_6$ carbon atoms when A represents N; or
R$^4$ and R$^5$ together represent a C$_2$–C$_5$ alkylene group when A represents N; or
R$^4$ and R$^5$ together represent a C$_2$–C$_5$ alkylene group containing NR$^{10}$ or NR$^{11}$ when A is CH or N, where R$^{10}$ is hydrogen or an alkyl group having $C_1$–$C_4$ carbon atoms and $R^{11}$ is an alkyl group having $C_1$–$C_4$ carbon atoms or

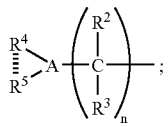

$R^7$ represents hydrogen or an alkyl or alkenyl group having $C_1$–$C_5$ carbon atoms;

$R^8$ represents an alkyl or alkenyl group having $C_4$–$C_{36}$ carbon atoms or —$COR^9$, where $R^9$ represents an alkyl or alkenyl group having $C_3$–$C_{35}$ carbon atoms; and n is an integer from 1 to 3, and where the compound is acid-blocked.

2. The compound of claim 1, wherein $R^1$ is hydrogen or

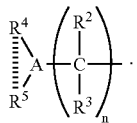

3. The compound of claim 1, wherein $R^2$ and $R^3$ are hydrogen.

4. The compound of claim 1, wherein $R^4$ and $R^5$ are alkyl groups having $C_1$–$C_6$ carbon atoms when A represents N.

5. The compound of claim 1, wherein $R^4$ and $R^5$ together represent —$CH_2CH_2N(CH_3)CH_2$—.

6. The compound of claim 1, wherein $R^7$ is hydrogen.

7. The compound of claim 1, wherein $R^8$ is an alkyl or alkenyl group having $C_4$–$C_{22}$ carbon atoms or —$COR^9$.

8. The compound of claim 1, wherein $R^9$ is an alkyl or alkenyl group having $C_3$–$C_{22}$ carbon atoms.

9. The compound of claim 1, wherein n is 2 or 3.

10. The compound of claim 1, wherein the compound is selected from the group consisting of N,N-bis-(3-dimethylaminopropyl)-N-(2-hydroxypropyl-octadecyl ether) amine, N-(3-dimethylaminopropyl)-N-(2-hydroxypropyl-octadecyl ether) amine, N,N-bis-(3-dimethylaminopropyl)-N-(2-hydroxypropyl-hexadecyl ether) amine, N-(3-dimethylaminopropyl)-N-(2-hydroxypropyl-hexadecyl ether) amine, N,N-bis-(3-dimethylaminopropyl)-N-(2-hydroxypropyl-tetradecyl ether) amine, N-(3-dimethylaminopropyl)-N-(2-hydroxypropyl-tetradecyl ether) amine, N,N-bis-(3-dimethylaminopropyl)-N-(2-hydroxypropyl-dodecyl ether) amine, N-(3-dimethylaminopropyl)-N-(2-hydroxypropyl-dodecyl ether) amine, N,N-bis-(3-dimethylaminopropyl)-N-(2-hydroxypropyl-decyl ether) amine, N-(3-dimethylaminopropyl)-N-(2-hydroxypropyl-decyl ether) amine, N,N-bis-(3-dimethylaminopropyl)-N-(2-hydroxypropyl-octyl ether) amine, N-(3-dimethylaminopropyl)-N-(2-hydroxypropyl-octyl ether) amine, N,N-bis-(3-dimethylaminopropyl)-N-(2-hydroxypropyl-2-ethylhexyl ether) amine, N-(3-dimethylaminopropyl)-N-(2-hydroxypropyl-2-ethylhexyl ether) amine, N,N-bis-(3-dimethylaminopropyl)-N-(2-hydroxypropyl-hexyl ether) amine, N-(3-dimethylaminopropyl)-N-(2-hydroxypropyl-hexyl ether) amine, N,N-bis-(3-dimethylaminopropyl)-N-(2-hexanol) amine, N-(3-dimethylaminopropyl)-N-(2-hexanol) amine, N,N-bis-(3-dimethylaminopropyl)-N-(2-octanol) amine, N-(3-dimethylaminopropyl)-N-(2-octanol) amine, N,N-bis-(3-dimethylaminopropyl)-N-(2-decanol) amine, N-(3-dimethylaminopropyl)-N-(2-decanol) amine, N,N-bis-(3-dimethylaminopropyl)-N-(2-dodecanol) amine, N-(3-dimethylaminopropyl)-N-(2-dodecanol) amine, N,N-bis-(3-dimethylaminopropyl)-N-(2-tetradecanol) amine, N-(3-dimethylaminopropyl)-N-(2-tetradecanol) amine, N,N-bis-(3-dimethylaminopropyl)-N-(2-hexadecanol) amine, N-(3-dimethylaminopropyl)-N-(2-hexadecanol) amine, N,N-bis-(3-dimethylaminopropyl)-N-(2-octadecanol) amine, N-(3-dimethylaminopropyl)-N-(2-octadecanol) amine; N,N-bis-(3-dimethylaminopropyl)-N-(2-hydroxypropyl butyl ether) amine; and N,N-bis-(3-dimethylaminopropyl)-N-(2-hydroxypropyl-neodecanoic ester) amine.

11. The compound of claim 10, wherein the compound is selected from the group consisting of N,N-bis-(3-dimethylaminopropyl)-N-(2-hydroxypropyl-octadecyl ether) amine, N-(3-dimethylaminopropyl)-N-(2-hydroxypropyl-octadecyl ether) amine, N,N-bis-(3-dimethylaminopropyl)-N-(2-hydroxypropyl-hexadecyl ether) amine, N-(3-dimethylaminopropyl)-N-(2-hydroxypropyl-hexadecyl ether) amine, N,N-bis-(3-dimethylaminopropyl)-N-(2-hydroxypropyl-tetradecyl ether) amine, N-(3-dimethylaminopropyl)-N-(2-hydroxypropyl-tetradecyl ether) amine, N,N-bis-(3-dimethylaminopropyl)-N-(2-hydroxypropyl-dodecyl ether) amine, N-(3-dimethylaminopropyl)-N-(2-hydroxypropyl-dodecyl ether) amine, N,N-bis-(3-dimethylaminopropyl)-N-(2-hydroxypropyl-decyl ether) amine, N-(3-dimethylaminopropyl)-N-(2-hydroxypropyl-decyl ether) amine, N,N-bis-(3-dimethylaminopropyl)-N-(2-hydroxypropyl-octyl ether) amine, N-(3-dimethylaminopropyl)-N-(2-hydroxypropyl-octyl ether) amine, N,N-bis-(3-dimethylaminopropyl)-N-(2-hydroxypropyl-2-ethylhexyl ether) amine, N-(3-dimethylaminopropyl)-N-(2-hydroxypropyl-2-ethylhexyl ether) amine, N,N-bis-(3-dimethylaminopropyl)-N-(2-hydroxypropyl-hexyl ether) amine, N-(3-dimethylaminopropyl)-N-(2-hydroxypropyl-hexyl ether) amine; N,N-bis-(3-dimethylaminopropyl)-N-(2-hydroxypropyl butyl ether) amine; and N,N-bis-(3-dimethylaminopropyl)-N-(2-hydroxypropyl-neodecanoic ester) amine.

12. The compound of claim 11, wherein the compound is N,N-bis-(3-dimethylaminopropyl)-N-(2-hydroxypropyl butyl ether) amine.

13. The compound of claim 11, wherein the compound is N,N-bis-(3-dimethylaminopropyl)-N-(2-hydroxypropyl-2-ethylhexyl ether) amine.

14. The compound of claim 11, wherein the compound is N,N-bis-(3-dimethylaminopropyl)-N-(2-hydroxypropyl-tetradecyl ether) amine.

15. The compound of claim 11, wherein the compound is N,N-bis-(3-dimethylaminopropyl)-N-(2-hydroxypropyl-dodecyl ether) amine.

16. The compound of claim 11, wherein the compound is N,N-bis-(3-dimethylaminopropyl)-N-(2-hydroxypropyl-neodecanoic ester) amine.

17. The compound of claim 11, wherein the compound is a mixture of N,N-bis-(3-dimethylaminopropyl)-N-(2-hydroxypropyl-tetradecyl ether) amine and N,N-bis-(3-dimethylaminopropyl)-N-(2-hydroxypropyl-dodecyl ether) amine.

18. The compound of claim 1 in which the composition is acid-blocked with a carboxylic acid.

19. The compound of claim 18 in which the carboxylic acid is formic acid, acetic acid, 2-ethyl-hexanoic acid, gluconic acid, or N-(2-hydroxyethyl)-iminodiacetic acid.

* * * * *